United States Patent [19]
Wolf et al.

[11] Patent Number: 5,698,416
[45] Date of Patent: Dec. 16, 1997

[54] METHODS FOR PRODUCTION OF ANTIGENS UNDER CONTROL OF TEMPERATURE-REGULATED PROMOTORS IN ENTERIC BACTERIA

[75] Inventors: Marcia K. Wolf, Silver Spring; Frederick J. Cassels, Ellicott City; Brian A. Bell, Clarksburg, all of Md.

[73] Assignee: The United States of America as represented by the Secretary of the Army, Washington, D.C.

[21] Appl. No.: 460,739

[22] Filed: Jun. 2, 1995

[51] Int. Cl.$^6$ .............................. C12P 21/06; C12N 1/20
[52] U.S. Cl. ................. 435/69.1; 435/71.2; 435/252.33
[58] Field of Search ........................... 435/69.1, 71.2, 435/252.33

[56] References Cited

PUBLICATIONS

Bergey's Manual of Sytematic Bacteriology, vol. 1. Krieg et al., eds.Williams & Wilkins: Baltimore, Maryland, pp. 414–417, 1984.

Qoronfleh et al. Journal of Bacteriology, 174(24):7902–7909, 1992.
Cowing et al. Proceedings of the National Academy of Sciences USA, 82:2679–2683, 1985.
Grewal et al. Journal of Clinical Microbiology, 32(5):1295–1301, 1994.
Maniatis et al. Molecular Cloning: A Laboratory Manual, pp.61–63, 68–73, and 88–92, 1982.
Sambrook et al. Molecular Cloning: A Laboratory Manual, Second Edition, pp. 18.30–18.41, 1989.

*Primary Examiner*—Douglas W. Robinson
*Assistant Examiner*—Thanda Wai
*Attorney, Agent, or Firm*—John Francis Moran

[57] ABSTRACT

Production of proteins in bacteria containing DNA sequences encoding proteins under the control of a temperature-regulated promotor is improved by growing the organisms at temperatures of less than 35° C. until the late logarithmic phase. Thereafter the temperature may be raised to 36° C. to 39° C. Antigens produced by the method of the invention may be used as vaccines, as means for measuring efficacy of vaccines, as probes to detect antigens from clinical samples and for biochemical characterization of antigens.

10 Claims, No Drawings

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 4875 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: DNA for CS6 protein ( x i ) SEQUENCE DESCRIPTION: SEQ ID NO:1:

| | | | | | | |
|---|---|---|---|---|---|---|
| AAGCTTGTAA | CCAGTTGATA | AAAATATATC | ACGCTGGGAA | TGACGTGATG | TATATACGGA | 60 |
| GCAGCTATGT | CGGAACAGAT | ATTTTCCTAT | CGGTATGCGT | TGTGAGTAAG | CGTAAAGCCA | 120 |
| ATGCTGTCTG | TAACTCCTGA | TCCTTGCAGA | CTAAATTAGA | GCTCCTTCTA | AATTAGACGG | 180 |
| ATGGATAAAC | CTACAGACTG | GCGCTCTGGG | TCTCGCCGGA | TATTTCTAA | TGAATTTAAG | 240 |
| CTTCATATGG | TTGAACTGGC | TTCGAAACCA | AATGCCAATG | TCGCACAACT | GGCTCGGGAA | 300 |
| CATGGCGTTG | ATAACAACCT | GATTTTAAA | TAGCTACGCC | TCTGGCAAAG | AGAAGGACGT | 360 |
| ATTTCTCGTA | GAATGCCTCC | AACTATTGTA | GGCCCTACAG | TACCACTGAG | GTAGCCTGAA | 420 |
| TTTAAAGCCG | AAGCGGTCAG | AACTGTTCTT | GGTGTGAACG | TAGCACTCAC | CAATAAAAGC | 480 |
| ATCAATACGG | TGCTCTGTTG | ACACATTACG | AATGTTATGT | ATACAATAAA | AATGATTATA | 540 |
| GCAATATTAA | TGGTGTTATA | TGAAGAAAAC | AATTGGTTTA | ATTCTAATTC | TTGCTTCATT | 600 |
| CGGCAGCCAT | GCCAGAACAG | AAATAGCGAC | TAAAAACTTC | CCAGTATCAA | CGACTATTTC | 660 |
| AAAAAGTTTT | TTTGCACCTG | AACCACGAAT | ACAGCCTTCT | TTTGGTGAAA | ATGTTGGAAA | 720 |
| GGAAGGAGCT | TTATTATTTA | GTGTGAACTT | AACTGTTCCT | GAAAATGTAT | CCCAGGTAAC | 780 |
| GGTCTACCCT | GTTTATGATG | AAGATTATGG | GTTAGGACGA | CTAGTAAATA | CCGCTGATGC | 840 |
| TTCCCAATCA | ATAATCTACC | AGATTGTTGA | TGAGAAAGGG | AAAAAAATGT | TAAAAGATCA | 900 |
| TGGTGCAGAG | GTTACACCTA | ATCAACAAAT | AACTTTTAAA | GCGCTGAATT | ATACTAGCGG | 960 |
| GGAAAAAAAA | ATATCTCCTG | GAATATATAA | CGATCAGGTT | ATGGTTGGTT | ACTATGTAAA | 1020 |
| CTAAATACTG | GAAGTATGAT | TATGTTGAAA | AAAATTATTT | CGGCTATTGC | ATTAATTGCA | 1080 |
| GGAACTTCCG | GAGTGGTAAA | TGCAGGAAAC | TGGCAATATA | AATCTCTGGA | TGTAAATGTA | 1140 |
| AATATTGAGC | AAAATTTTAT | TCCAGATATT | GATTCCGCTG | TTCGTATAAT | ACCTGTTAAT | 1200 |
| TACGATTCGG | ACCCGAAACT | GGATTCACAG | TTATATACGG | TTGAGATGAC | GATCCCTGCA | 1260 |
| GGTGTAAGCG | CAGTTAAAAT | CGCACCAACA | GATAGTCTGA | CATCTTCTGG | ACAGCAGATC | 1320 |
| GGAAAGCTGG | TTAATGTAAA | CAATCCAGAT | CAAAATATGA | ATTATTATAT | CAGAAAGGAT | 1380 |
| TCTGGCGCTG | GTAACTTTAT | GGCAGGACAA | AAAGGATCCT | TTCCTGTCAA | AGAGAATACG | 1440 |
| TCATACACAT | TCTCAGCAAT | TTATACTGGT | GGCGAATACC | CTAATAGCGG | ATATTCGTCT | 1500 |
| GGTACTTATG | CAGGAAATTT | GACTGTATCA | TTTTACAGCA | ATTAAAAAAA | GGCCGCATTA | 1560 |
| TTGCGGCCAT | TGACGATACT | GCTAGGCAAA | AATGAAAT | CAAAGTTAAT | TATACTATTG | 1620 |
| ACGTTAGTGC | CATTTTCATC | TTTTTCAACA | GGAAATAATT | TTGAAATAAA | TAAGACACGA | 1680 |
| GTAATTTACT | CTGACAGCAC | ACCATCAGTT | CAAATATCAA | ATAATAAAGC | ATATCCTTTA | 1740 |
| ATTATTCAAA | GCAATGTATG | GGATGAAAGC | AATAATAAAA | ATCATGACTT | TATAGCAACA | 1800 |
| CCACCGATTT | TTAAAATGGA | AAGTGAAAGT | CGGAATATAA | TAAAAATAAT | TAAAACAACT | 1860 |
| ATTAATTTGC | CGGACTCTCA | GGAAAGTATG | AGATGGTTAT | GTATTGAATC | AATGCCACCA | 1920 |
| ATAGAAAAAA | GTACTAAAAT | AAACAGAAAA | GAAGGAAGGA | CAGACAGTAT | TAATATCAGC | 1980 |
| ATTCGGGGGT | GCATTAAACT | GATATATCGA | CCTGCCAGTG | TTCCGTCTCC | TGTTTTTAAT | 2040 |
| AATATAGTAG | AAAAATTAAA | ATGGCATAAA | AATGGAAAGT | ATCTTGTATT | AAAAAATAAT | 2100 |
| ACACCCTATT | ACATTAGCTT | TTCTGAGGTT | TTTTTGATT | CAGATAAAGT | AAACAATGCA | 2160 |
| AAAGATATTT | TATATGTAAA | ACCATACTCA | GAGAAGAAAA | TAGATATCAG | CAACAGAATA | 2220 |

```
ATAAAAAAAA TCAAATGGGC TATGATTGAT GATGCTGGCG CAAAAACAAA ACTTTATGAA    2280
TCAATTTTAT AAAAAATCTC ATTACAGTAT ACAAAAACAT CAGATTACAG GCTTGCTTTT    2340
TTTGCTATTT ATATATCCTT TCTCAACCTC ATATGGAAAT GAACAATTTA GTTTGACTC     2400
ACGATTCCTA CCATCAGGTT ATAATTACTC TTTAAATAGT AACTTACCTC CTGAAGGTGA    2460
GTATCTGGTT GATATTTATA TTAACAAAAT AAAAAAGGAG TCCGCGATTA TTCCTTTTTA    2520
TATAAAAGGA AATAAACTTG TACCATGTTT ATCAAAGAA AAAATTTCAT CTTTGGGTAT     2580
CAACATTAAT AATAACGACA ACACAGAGTG TGTAGAAACA AGTAAGGCAG GTATTAGTAA    2640
TATCAGCTTT GAGTTAGCT CTCTTCGTTT GTTATTGCT GTACCGAAAA ATCTTCTGTC      2700
TGAGATTGAT AAAATATCAT CAAAGGATAT AGATAACGGG ATTCATGCTT TATTTTTAA     2760
TTATCAAGTA AATACAAGGC TAGCCAATAA TAAAAATCGT TATGATTACA TTTCTGTTTC    2820
ACCAAATATA AATTATTTTT CATGGCGGTT GCGTAATCTT TTTGAATTTA ACCAAAACAA    2880
CGATGAAAAA ACATGGGAAA GAAACTACAC TTATCTAGAA AAAGTTTTT ATGATAAAAA     2940
GCTAAACTTA GTCGTTGGTG AAAGTTATAC GAATTCAAAT GTTATAATA ACTACTCTTT     3000
TACTGGTATT TCAGTTCTA CAGATACAGA TATGTATACG CCAAGTGAAA TCGATTATAC     3060
ACCAGAAATT CATGGAGTGG CTGATTCAGA CTCTCAGATT ATTGTCAGGC AAGGCAACAC    3120
CATTATCATT AATGAAAGTG TTCCAGCCGG ACCGTTCTCA TTTCCAATAA CCAATCTCAT    3180
GTATACTGGG GGGCAACTTA ATGTGGAGAT AACAGATATT TATGGAAATA AAAAACAATA    3240
TACTGTCAAT AATTCCTCTC TTCCTGTTAT GAGAAAAGCG GGACTAATGG TATATAATTT    3300
TATATCTGGG AAATTAACAA AAAAAAATAG TGAGGATGGT GATTTTTTA CTCAAGGTGA     3360
TATTAACTAC GGTACTCACT ATAACAGCAC ACTATTCGGT GGATATCAGT TTAGTAAAAA    3420
TTATTTTAAC TTATCTACTG GTATAGGCAC TGATCTGGGA TTTTCTGGAG CATGGCTACT    3480
ACACGTTAGC AGAAGTAATT TTAAGAATAA AAATGGATAT AATATTAATC TACAACAAAA    3540
CACTCAGTTA AGACCATTCA ATGCCGGGGT TAATTTCGAT TACGCATACA GAAAAAAAG    3600
GTATGTGGAA CTTTCCGACA TTGGCTGGCA TGGTAATTTA TATAATCAAC TTAAAAATAG    3660
TTTTTCTTTA TCCTTGTCAA AATCATTGAA TAAATACGGA AATTTCTCAC TTGATTATAA    3720
CAAAATGAAA TACTGGGATA ATGCGTATGA TAGTAACTCA ATGTCGATTC GTTATTTTTT    3780
TAAATTCATG CGAGCAATGA TTACAACAAA TTGTTCTTTA AATAAATATC AATCTTATGA    3840
AAAAAAAGAT AAAAGATTTA GTATTAATAT ATCATTGCCT TTAACCAAAG ATTACGGGCA    3900
CATATCTTCA AACTATTCAT TTTCCAATGC AAATACAGGA ACGGCAACCA GTTCTGTAGG    3960
CTTAAACGGT AGTTTTTTA ATGACGCAAG ATTAAACTGG AACATTCAGC AGAACAGAAC     4020
GACCCGTAAC AATGGATATA CTGATAATAC CAGTTACATA GCAACCAGCT ATGCCTCTCC    4080
CTATGGCGTT TTTACTGGTT CATATTCAGG ATCGAACAAG TATTCAAGCC AGTTTATTC     4140
TGCATCGGGA GGTATTGTTT TGCATAGCGA TGGCGTAGCT TTTACTCAAA AAGCCGGAGA    4200
TACCTCTGCT CTTGTCCGTA TTGATAATAT TTCTGATATA AAAATTGGTA ACACTCCTGG    4260
TGTTTATACT GGGTATAATG GTTTGCTTT AATTCCTCAT CTTCAGCCGT TCAAAAAAA     4320
CACCATTTTA ATTAATGATA AAGGAATTCC AGACGGTATT ACTCTTGCTA ATATAAAAAA    4380
ACAAGTTATC CCATCACGAG GAGCTATTGT TAAAGTAAAA TTTGATGCTA AAAAAGGCAA    4440
TGACATTTTG TTTAAGCTTA CAACTAAAGA TGGAAAAACG CCCCCATTAG GAGCTATAGC    4500
CCATGAAAAA AATGGAAAAC AGATTAATAC GGGTATCGTT GACGATGATG GTATGCTTTA    4560
TATGTCTGGA TTATCAGGGA CAGGGATTAT TAATGTAACA TGGAATGGAA AAGTCTGTTC    4620
```

```
ATTTCCTTTT TCAGAAAAAG ATATATCTAG CAAACAATTA TCTGTTGTAA ATAAACAATG         4680

TTAGGTAGTG CATCCAATTA GTAGAACATG TGTTTTTCGA TAAACGCTCC GATCTCTTTT         4740

TCGTGGATCT CAACTGAGCG TGAGAAGCAG ATTGTTTTAC GAGCCAACCG CTTAATGCGG         4800

GTGCGTAGCG TCAGATTATT ACGCTCAATG CGTTGGGTGA ATATTTGCC GGTCAGATGC          4860

TTATTCTTCG GTACC                                                         4875
```

( 2 ) INFORMATION FOR SEQ ID NO:2:

( i ) SEQUENCE CHARACTERISTICS:
        ( A ) LENGTH: 512 base pairs
        ( B ) TYPE: nucleic acid
        ( C ) STRANDEDNESS: double
        ( D ) TOPOLOGY: unknown ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: DNA for encoding CFA1 protein ( x i ) SEQUENCE DESCRIPTION: SEQ ID NO:2:

```
ATGAAATTTA AAAAAACTAT TGGTGCAATG GCTCTGACCA CAATGTTTGT AGCAGTGAGT          60

GCTTCAGCAG TAGAGAAAAA TATTACTGTA ACAGCTAGTG TTGATCCTGT AATTGATCTT         120

TGCAAGCTGA TGGCAATGCT CTGCCATCAG CTGTAAAGTT AGCTTATTCT CCCGCATCAA         180

AAACTTTTGA AAGTTACAGA GTAATGACTC AAGTTCATAC AAACGATGCA ACTAAAAAAG         240

TAATTGTTAA ACTTGCTGAT ACACCACAGC TTACAGATGT TCTGAATTCA ACTGTTCAAA         300

TGCCTATCAG TGTGTCATGG GGAGGACAAG TATTATCTAC AACAGCCAAA GAATTTGAAG         360

CTGCTGCTTT GGGATATTCT GCATCCGGTG TAAATGGCGT ATCATCTTCT CAAGAGTTAG         420

TAATTAGCGC TGCACCTAAA ACTGCCGGTA CCGCCCCAAC TGCAGGAAAC TATTCAGGAG         480

TAGTATCTCT TGTAATGACT TTGGGATCCT GA                                      512
```

( 2 ) INFORMATION FOR SEQ ID NO:3:

( i ) SEQUENCE CHARACTERISTICS:
        ( A ) LENGTH: 170 amino acids
        ( B ) TYPE: amino acid
        ( C ) STRANDEDNESS: unknown
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: CFA1 protein ( x i ) SEQUENCE DESCRIPTION: SEQ ID NO:3:

```
Met Lys Phe Lys Lys Thr Ile Gly Ala Met Ala Leu Thr Thr Met Phe
  1           5                  10                  15

Val Ala Val Ser Ala Ser Ala Val Glu Lys Asn Ile Thr Val Thr Ala
             20                  25                  30

Ser Val Asp Pro Val Ile Asp Leu Leu Gln Ala Asp Gly Asn Ala Leu
             35                  40                  45

Pro Ser Ala Val Lys Leu Ala Tyr Ser Pro Ala Ser Lys Thr Phe Glu
 50                  55                  60
```

```
Ser  Tyr  Arg  Val  Met  Thr  Gln  Val  His  Thr  Asn  Asp  Ala  Thr  Lys  Lys
 65                  70                      75                       80

Val  Ile  Val  Lys  Leu  Ala  Asp  Thr  Pro  Gln  Leu  Thr  Asp  Val  Leu  Asn
                85                      90                            95

Ser  Thr  Val  Gln  Met  Pro  Ile  Ser  Val  Ser  Trp  Gly  Gly  Gln  Val  Leu
               100                     105                      110

Ser  Thr  Thr  Ala  Lys  Glu  Phe  Glu  Ala  Ala  Ala  Leu  Gly  Tyr  Ser  Ala
          115                     120                      125

Ser  Gly  Val  Asn  Gly  Val  Ser  Ser  Gln  Glu  Leu  Val  Ile  Ser  Ala
     130                     135                    140

Ala  Pro  Lys  Thr  Ala  Gly  Thr  Ala  Pro  Thr  Ala  Gly  Asn  Tyr  Ser  Gly
145                      150                    155                       160

Val  Val  Ser  Leu  Val  Met  Thr  Leu  Gly  Ser
               165                      170
```

(2) INFORMATION FOR SEQ ID NO:4:

(i) SEQUENCE CHARACTERISTICS:
        (A) LENGTH: 504 base pairs
        (B) TYPE: nucleic acid
        (C) STRANDEDNESS: double
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (A) ORGANISM: DNA which encodes CS3 protein (xi) SEQUENCE DESCRIPTION: SEQ ID NO:4:

```
ATGTTAAAAA  TAAAATACTT  ATTAATAGGT  CTTTCACTGT  CAGCTATGAG  TTCATACTCA    60

CTAGCTGCAG  CGGGGCCCAC  TCTAACCAAA  GAACTGGCAT  TAAATGTGCT  TTCTCCTGCA   120

GCTCTGGATG  CAACTTGGGC  TCCTCAGGAT  AATTTAACAT  TATCCAATAC  TGGCGTTTCT   180

AATACTTTGG  TGGGTGTTTT  GACTCTTTCA  ATACCAGTA   TTGATACAGT  TAGCATTGCG   240

AGTACAAGTG  TTTCTGATAC  ATCTAAGAAT  GGTACAGTAA  CTTTTGCACA  TGAGACAAAT   300

AACTCTGCTA  GCTTTGCCAC  CACCATTTCA  ACAGATAATG  CCAACATTAC  GTTGGATAAA   360

AATGCTGGAA  ATACGATTGT  TAAAACTACA  AATGGGAGTC  AGTTGCCAAC  TAATTTACCA   420

CTTAAGTTTA  TTACCACTGA  AGGTAACGAA  CATTTAGTTT  CAGGTAATTA  CCGTGCAAAT   480

ATAACAATTA  CTTCGACAAT  TAAA                                            504
```

(2) INFORMATION FOR SEQ ID NO:5:

(i) SEQUENCE CHARACTERISTICS:
        (A) LENGTH: 168 amino acids
        (B) TYPE: amino acid
        (C) STRANDEDNESS: unknown
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Cs3 protein (xi) SEQUENCE DESCRIPTION: SEQ ID NO:5:

```
Met  Leu  Lys  Ile  Lys  Tyr  Leu  Leu  Ile  Gly  Leu  Ser  Leu  Ser  Ala  Met
```

-continued

| 1 | | | | 5 | | | | | 10 | | | | | 15 | |
|---|---|---|---|---|---|---|---|---|---|---|---|---|---|---|---|
| Ser | Ser | Tyr | Ser | Leu | Ala | Ala | Ala | Gly | Pro | Thr | Leu | Thr | Lys | Glu | Leu |
| | | | 20 | | | | | 25 | | | | | 30 | | |
| Ala | Leu | Asn | Val | Leu | Ser | Pro | Ala | Ala | Leu | Asp | Ala | Thr | Trp | Ala | Pro |
| | | 35 | | | | | 40 | | | | | 45 | | | |
| Gln | Asp | Asn | Leu | Thr | Leu | Ser | Asn | Thr | Gly | Val | Ser | Asn | Thr | Leu | Val |
| | 50 | | | | | 55 | | | | | 60 | | | | |
| Gly | Val | Leu | Thr | Leu | Ser | Asn | Thr | Ser | Ile | Asp | Thr | Val | Ser | Ile | Ala |
| 65 | | | | | 70 | | | | | 75 | | | | | 80 |
| Ser | Thr | Ser | Val | Ser | Asp | Thr | Ser | Lys | Asn | Gly | Thr | Val | Thr | Phe | Ala |
| | | | | 85 | | | | | 90 | | | | | 95 | |
| His | Glu | Thr | Asn | Asn | Ser | Ala | Ser | Phe | Ala | Thr | Thr | Ile | Ser | Thr | Asp |
| | | | 100 | | | | | 105 | | | | | 110 | | |
| Asn | Ala | Asn | Ile | Thr | Leu | Asp | Lys | Asn | Ala | Gly | Asn | Thr | Ile | Val | Lys |
| | | 115 | | | | | 120 | | | | | 125 | | | |
| Thr | Thr | Asn | Gly | Ser | Gln | Leu | Pro | Thr | Asn | Leu | Pro | Leu | Lys | Phe | Ile |
| | 130 | | | | | 135 | | | | | 140 | | | | |
| Thr | Thr | Glu | Gly | Asn | Glu | His | Leu | Val | Ser | Gly | Asn | Tyr | Arg | Ala | Asn |
| 145 | | | | | 150 | | | | | 155 | | | | | 160 |
| Ile | Thr | Ile | Thr | Ser | Thr | Ile | Lys | | | | | | | | |
| | | | | 165 | | | | | | | | | | | |

METHODS FOR PRODUCTION OF ANTIGENS UNDER CONTROL OF TEMPERATURE-REGULATED PROMOTORS IN ENTERIC BACTERIA

FIELD OF THE INVENTION

This invention is related to the preparation of proteins. The method has been found to be particularly useful for the preparation of antigens in *E. coli*. The natural and recombinant constructs giving rise to the proteins contain temperature-regulated promotors. The methods of the invention are exemplified by the production of antigens classified as colonization factor antigens (CFA) which have use as vaccines and for giving rise to antibodies for laboratory testing for antigens.

BACKGROUND OF THE INVENTION

Colonization factor antigens (CFA) are an important class of antigens which influence the ability of pathogenic organisms to colonize in the host organism. In both the natural and in recombinant organisms, the production of these antigens is under the control of temperature-regulated promotors. Previous methods for large-scale production of such antigens have been unsatisfactory. Many methods were practiced using solid media. The prior art methods resulted in low yield of bacteria and of the desired CFA antigens. Furthermore, there was great risk of contamination of the desired products using the prior art methods. The previously disclosed methods recite incubation for bacterial growth at 37° C.

Most reports of production of colonization factor antigens teach use of solid media. The instantly taught inventive method for optimization of production has not previously been disclosed. One of the most useful proteins produced under the control of a temperature-regulated promotor is the CS6 component of CFA/IV (colonization factor antigen IV), one of three CFAs commonly found on enterotoxigenic *Escherichia coli* (ETEC). A recent study showed CS6 on 31% of ETEC isolated from soldiers in the Middle East. Other CFAs and similar proteins found on the surface of ETEC function as adhesins to attach bacteria to intestinal epithelial cells. Attached bacteria can then deliver their toxin(s) to the target cells. It has never been proved that CS6 is an adhesin for human tissue (Knutton, S., M. M. McConnell, B. Rowe, and A. S. McNeish, "Adhesion and ultrastructural properties of human enterotoxigenic *Escherichia coli* producing colonization factor antigens III and IV", *Infect. Immun.* 57:3364–3371 (1989)), but a study in rabbits indicated CS6 is a colonization factor and has been shown to be responsible for adherence to culture HeLa cells. (See Guth, B. E. C., E. G. Aguiar, P. M. Griffin, S. R. T. D. Ramos, and T. A. T. Gomes. 1994. Prevalence of colonization factor antigens (CFAs) and adherence to HeLa cells in enterotoxigenic *Escherichia coli* isolated from feces of children in Sa o Paulo", *Microbiol. Immunol.* 38: 695–701.)

Other proteins having much in common with the CS6 operon are known and include fimbrial operons from *E. coli*, Salmonella, Yersinia, Klebsiella, Haemophilus, and Bordetella. All contain molecular chaperones and ushers and a number of structural subunits. Temperature regulation of CS6 expression is characteristic of CS6 and of other CFA's from enterotoxigenic *E. coli* (ETEC) and virulence genes in a variety of pathogenic bacteria.

The availability of improved methods for preparation of antigens is increasingly important as travel may expose persons to organisms which seldom cause serious pathology in persons who are native to the area where infections are endemic. Furthermore, the weakening of persons during natural disasters which is often accompanied by increased exposure to contaminated water and food often results in serious illness in the population, particularly in children and in the elderly. Hence, there is need for improved methods for the production of antigens for use as vaccines against effects of exposure to contaminated food or drink.

SUMMARY OF THE INVENTION

The method of the invention comprises growing bacteria containing DNA sequences encoding proteins under the control of a temperature-regulated promotor in a broth containing tryptone and yeast extract wherein the temperature of the broth is kept at less than 35° C. but more than 20° C. until the late logarithmic phase. Bacteria are separated from the media followed by purification of the desired proteins. A more preferred temperature range for growth before the late logarithmic phase is 25° C. to 33° C., with best results seen when broth was kept under fermentation conditions at 30° C. to 33° C. either until the late logarithmic phase or throughout the fermentation process. During the late logarithmic phase the temperature may be raised to temperatures in the range of 36° C.–39° C.

DETAILED DESCRIPTION OF THE INVENTION

This invention provides means of producing easily purified proteins under the control of temperature-regulated promotors inexpensively. The antigens produced by the methods of the invention can also be used for measuring the efficacy of vaccines under development, as probes to detect antigens from clinical samples, and for biochemical characterization of antigens.

The processes of the invention are particularly applicable to the production of CFAs. While certain specific proteins have been identified and the process is exemplified using a bacteria which contains a DNA sequence of CS6 wherein the appropriate genes have been introduced into *Escherichia coli* bacterial strain HB101, ATCC deposit number 33694, the methods taught herein can be used for production of other proteins wherein the DNA sequence encoding the protein is under the control of a temperature-regulated promotor.

MATERIALS AND METHODS

The fermenter was a Bioflow III fermenter with a 6.6 liter glass vessel (5 liter working volume). The media used in the example was prepared using Luria broth media at 2× concentration with 0.4% glycerol and containing 100 g tryptone, 50 g yeast extract, 100 g NaCl, 20 ml glycerol. The tryptone and yeast extracts were obtained from Difco Laboratories, Detroit, Mich. The L broth (2×) contained twice the concentration of the original recipe by Luria. The broth was adjusted to provide a total volume of 5 liters. The media was then autoclaved. After the media had cooled to approximately 45° C., ampicillin was added to provide a concentration of 50 µg/l. An inoculum of about $3.2 \times 10^9$ bacterial cells per milliliter, said bacteria containing the desired DNA insert (see Table I), was added.

The media containing the desired proteins was purified using membrane filtration and ultrafiltration, though any separation method known in the art for purifying proteins from spent media would be appropriate. Filtration apparatus was obtained from Sartorius (Edgewood, N.Y.) using the Sarticon-Mini MF and UF systems following the directions of the manufacturer. In the filtration process, the manufacturer's instructions were followed. During the membrane filtration (0.2 µm membrane used), the initial pass run was 15 minutes. Inlet pressure was 9.5–10 psi, outlet pressure was 0 (open). Permeate pressure was 3 psi, cross-flow velocity was about 1 liter/minute, and flux was about 200 ml/min. This buffer wash was run using phosphate buffered saline (PBS) with wash volume of 1.7 liters at a run time of about 20 minutes. Inlet pressure was 8 psi, outlet pressure was 0 (open), permeate pressure was 2 psi with retentate volume of 500 ml and permeate volume of 4 liters.

The ultrafiltration was run using Sariton Mini system with 100,000 molecular weight cut-off to purify filtrate obtained above. On the initial pass run, the run time was 21 minutes. Run parameters: Inlet pressure=6–10 psi, outlet pressure=2–3 psi, permeate pressure=0, cross-flow velocity about 1 liter/min, and flux=168–210 ml/min. A buffer wash with PBS was run for about 10 minutes. Run parameters: inlet pressure=6–10 psi, outlet pressure=0–1.5 psi, permeate pressure=0, wash volume=3 liters, retentate volume=480 ml, and permeate volume=6.5 liters. The rententate of ultrafiltration run contained the desired protein.

Fermentation for production of CS6 from bacteria containing the desired DNA insert was effected at a temperature of 30° C.–33° C. with agitation provided by stirring at 200 RPM in the presence of free running oxygen. (No dissolved oxygen probe was used.)

It has been the practice in the prior art methods to produce proteins at 37° C. Those prior art conditions, when used to produce some proteins, may cause rapid initial production of protein followed by early death of cells. The early death of cells can result in limited production of the desired protein. It is, therefore, the purpose of this invention to provide a means of producing large amounts of protein in broth by provision of sufficient nutrients to facilitate protein production at temperatures which allow for increased survival time for the cells producing the desired proteins.

EXAMPLE 1

Recombinant bacteria were constructed by introducing cloned CS6 genes into *E. coli* bacterial strain HB101 (ATCC #33694). (See Table I.) An inoculum of about $4.7 \times 10^{10}$ bacteria was introduced into Luria broth media at 32° C. The temperature of the bacterial culture was increased to 37° C. only when growth was in the late logarithmic phase ($A_{600}$ of 1.4). Bacteria were removed from the media by filtration. Then, the CS6 protein was recovered and concentrated from the spent media by membrane filtration.

When the desired protein is obtained from the bacteria rather than the supernatant, the bacterial membranes may be disrupted to release the desired proteins. For example, the bacteria may be sheared and the desired proteins obtained by 1) suspending the bacteria in a solution such as buffered or saline solution, 2) shearing the proteins (a blender may be used for this process), 3) removing the bacteria from the buffered or saline solution, then extracting the desired proteins from the buffered or saline solution. The bacteria may be suspended in solution such as buffered or saline solution, then ruptured. Methods known in the art include use of a press such as a French press. The bacteria may also be disrupted by chemical means. The bacterial debris is removed from the solution containing the lysed cells followed by recovery of the protein.

(While the example given here uses the Luria broth, it is possible to practice the process of the invention using other nutrient broths, so long as the broth contains both tryptone and yeast extract.)

The method of the invention reduces chances for contamination during the production process and reduces the large number of assays required for quality control when small aliquots are pooled to make a final product.

EXAMPLE 2

The process of example 1 was varied so that a temperature of 30° C. was maintained throughout the entire fermentation period. The bacteria were separated from the media by membrane filtration (0.22 μm polyether sulfone module of Saritcon-Mini). 2.8 liters of fermentation broth were processed by this method.

The CS6 was separated from the media proteins by ultrafiltration (100,000 molecular weight cut-off (MWCO) polysulfone module of Sarticon-Mini used in accord with the manufacturer's instructions). A 480 ml portion was retained which contained 0.61 mg/ml protein for a total protein of 293 mg. The protein had a purity of 70% for a yield of 73 mg CS6 having purity of 70% per liter of fermentation broth.

TABLE I

| | | | | | |
|---|---|---|---|---|---|
| aagcttgtaa | ccagttgata | aaaatatatc | acgctgggaa | tgacgtgatg | tatatacgga |
| gcagctatgt | cggaacagat | attttcctat | cggtatgcgt | tgtgagtaag | cgtaaagcca |
| atgctgtctg | taactcctga | tccttgcaga | ctaaattaga | gctccttcta | aattagacgg |
| atggataaac | ctacagactg | gcgctctggg | tctcgccgga | tattttctaa | tgaatttaag |
| cttcatatgg | ttgaactggc | ttcgaaacca | aatgccaatg | tcgcacaact | ggctcgggaa |
| catggcgttg | ataacaacct | gatttttaaa | tagctacgcc | tctggcaaag | agaaggacgt |
| atttctcgta | gaatgcctcc | aactattgta | ggccctacag | taccactgag | gtagcctgaa |
| tttaaagccg | aagcggtcag | aactgttctt | ggtgtgaacg | tagcactcac | caataaaagc |
| atcaatacgg | tgctctgttg | acacattacg | aatgttatgt | atacaataaa | aatgattata |
| gcaatattaa | tggtgttata | tgaagaaaac | aattggttta | attctaattc | ttgcttcatt |
| cggcagccat | gccagaacag | aaatagcgac | taaaaacttc | ccagtatcaa | cgactatttc |
| aaaaagtttt | tttgcacctg | aaccacgaat | acagccttct | tttggtgaaa | atgttggaaa |
| ggaaggagct | ttattattta | gtgtgaactt | aactgttcct | gaaaatgtat | cccaggtaac |
| ggtctaccct | gtttatgatg | aagattatgg | gttaggacga | ctagtaaata | ccgctgatgc |
| ttcccaatca | ataatctacc | agattgttga | tgagaaaggg | aaaaaaatgt | taaaagatca |
| tggtgcagag | gttacaccta | atcaacaaat | aacttttaaa | gcgctgaatt | atactagcgg |
| ggaaaaaaaa | atatctcctg | gaatatataa | cgatcaggtt | atggttggtt | actatgtaaa |
| ctaaatactg | gaagtatgat | tatgttgaaa | aaaattattt | cggctattgc | attaattgca |
| ggaacttccg | gagtggtaaa | tgcaggaaac | tggcaatata | aatctctgga | tgtaaatgta |
| aatattgagc | aaaattttat | tccagatatt | gattccgctg | ttcgtataat | acctgttaat |
| tacgattcgg | acccgaaact | ggattcacag | ttatatacgg | ttgagatgac | gatccctgca |
| ggtgtaagcg | cagttaaaat | cgcaccaaca | gatagtctga | catcttctgg | acagcagatc |

TABLE I-continued

| | | | | |
|---|---|---|---|---|
| ggaaagctgg | ttaatgtaaa | caatccagat | caaaatatga | attattatat | cagaaaggat |
| tctggcgctg | gtaactttat | ggcaggacaa | aaaggatcct | ttcctgtcaa | agagaatacg |
| tcatacacat | tctcagcaat | ttatactggt | ggcgaatacc | ctaatagcgg | atattcgtct |
| ggtacttatg | caggaaattt | gactgtatca | ttttacagca | attaaaaaaa | ggccgcatta |
| ttgcggccat | tgacgatact | gctaggcaaa | aatatgaaat | caaagttaat | tatactattg |
| acgttagtgc | cattttcatc | tttttcaaca | ggaaataatt | ttgaaataaa | taagacacga |
| gtaatttact | ctgacagcac | accatcagtt | caaatatcaa | ataataaagc | atatccttta |
| attattcaaa | gcaatgtatg | ggatgaaagc | aataataaaa | atcatgactt | tatagcaaca |
| ccaccgattt | ttaaaatgga | aagtgaaagt | cggaatataa | taaaaataat | taaacaact |
| attaatttgc | cggactctca | ggaaagtatg | agatggttat | gtattgaatc | aatgccacca |
| atagaaaaaa | gtactaaat | aaacagaaaa | gaaggaagga | cagacagtat | taatatcagc |
| attcggggt | gcattaaact | gatatatcga | cctgccagtg | ttccgtctcc | tgtttttaat |
| aatatagtag | aaaaattaaa | atggcataaa | aatggaaagt | atcttgtatt | aaaaaataat |
| acaccctatt | acattagctt | ttctgaggtt | tttttgatt | cagataaagt | aaacaatgca |
| aaagatattt | tatatgtaaa | accatactca | gagaagaaaa | tagatatcag | caacagaata |
| ataaaaaaaa | tcaaatgggc | tatgattgat | gatgctggcg | caaaaacaaa | acttatgaa |
| tcaatttat | aaaaaatctc | attacagtat | acaaaaacat | cagattacag | gcttgctttt |
| tttgctattt | atatatcctt | tctcaacctc | atatggaaat | gaacaattta | gtttgactc |
| acgattccta | ccatcaggtt | ataattactc | tttaaatagt | aacttaccc | ctgaaggtga |
| gtatctggtt | gatatttata | ttaacaaaat | aaaaaaggag | tccgcgatta | ttcctttta |
| tataaaagga | aataaacttg | taccatgttt | atcaaaagaa | aaaatttcat | ctttgggtat |
| caacattaat | aataacgaca | acacagagtg | tgtagaaaca | agtaaggcag | gtattagtaa |
| tatcagcttt | gagtttagct | ctcttcgttt | gtttattgct | gtaccgaaaa | atcttctgtc |
| tgagattgat | aaaatatcat | caaaggatat | agataacggg | attcatgctt | tattttttaa |
| ttatcaagta | aatacaaggc | tagccaataa | taaaaatcgt | tatgattaca | tttctgtttc |
| accaaaatata | aattattttt | catggcggtt | gcgtaatctt | tttgaattta | accaaaacaa |
| cgatgaaaaa | acatgggaaa | gaaactacac | ttatctagaa | aaagttttt | atgataaaaa |

TABLE I-continued

| | | | | |
|---|---|---|---|---|
| gctaaactta | gtcgttggtg | aaagttatac | gaattcaaat | gtttataata | actactcttt |
| tactggtatt | tcagtttcta | cagatacaga | tatgtatacg | ccaagtgaaa | tcgattatac |
| accagaaatt | catggagtgg | ctgattcaga | ctctcagatt | attgtcaggc | aaggcaacac |
| cattatcatt | aatgaaagtg | ttccagccgg | accgttctca | tttccaataa | ccaatctcat |
| gtatactggg | gggcaactta | atgtggagat | aacagatatt | tatggaaata | aaaaacaata |
| tactgtcaat | aattcctctc | ttcctgttat | gagaaaagcg | ggactaatgg | tatataattt |
| tatatctggg | aaattaacaa | aaaaaaatag | tgaggatggt | gatttttta | ctcaaggtga |
| tattaactac | ggtactcact | ataacagcac | actattcggt | ggatatcagt | ttagtaaaaa |
| ttattttaac | ttatctactg | gtataggcac | tgatctggga | ttttctggag | catggctact |
| acacgttagc | agaagtaatt | ttaagaataa | aaatggatat | aatattaatc | tacaacaaaa |
| cactcagtta | agaccattca | atgccggggt | taattttcgat | tacgcataca | gaaaaaaaag |
| gtatgtggaa | cttccgaca | ttggctggca | tggtaattta | tataatcaac | ttaaaaaatag |
| ttttctttta | tccttgtcaa | aatcattgaa | taaatacgga | aatttctcac | ttgattataa |
| caaaatgaaa | tactgggata | atgcgtatga | tagtaactca | atgtcgattc | gttattttt |
| taaattcatg | cgagcaatga | ttacaacaaa | ttgttctttta | aataaatatc | aatcttatga |
| aaaaaaagat | aaaagattta | gtattaatat | atcattgcct | ttaaccaaag | attacgggca |
| catatcttca | aactattcat | tttccaatgc | aaatacagga | acggcaacca | gttctgtagg |
| cttaaacggt | agtttttta | atgacgcaag | attaaactgg | aacattcagc | agaacagaac |
| gacccgtaac | aatggatata | ctgataatac | cagttacata | gcaaccagct | atgcctctcc |
| ctatggcgtt | tttactggtt | catattcagg | atcgaacaag | tattcaagcc | agttttattc |
| tgcatcggga | ggtattgttt | tgcatagcga | tggcgtagct | tttactcaaa | aagccggaga |
| tacctctgct | cttgtccgta | ttgataatat | ttctgatata | aaaattggta | acactcctgg |
| tgtttatact | gggtataatg | gttttgcttt | aattcctcat | cttcagccgt | tcaaaaaaa |
| caccatttta | attaatgata | aaggaattcc | agacggtatt | actcttgcta | atataaaaaa |
| acaagttatc | ccatcacgag | gagctattgt | taaagtaaaa | tttgatgcta | aaaaaggcaa |
| tgacattttg | tttaagctta | caactaaaga | tggaaaaccg | cccccattag | gagctatagc |
| ccatgaaaaa | aatggaaaac | agattaatac | gggtatcgtt | gacgatgatg | gtatgctta |

TABLE I-continued

| | | | | | |
|---|---|---|---|---|---|
| tatgtctgga | ttatcaggga | cagggattat | taatgtaaca | tggaatggaa | aagtctgttc |
| atttcctttt | tcagaaaaag | atatatctag | caaacaatta | tctgttgtaa | ataaacaatg |

The process of the invention can be used to produce other proteins by inserting other DNA sequences into the appropriate organism for production. For example, DNA sequences producing the following sequences may be inserted into the HB101 E. coli. (ATCC accession No. 33694).

Other examples of proteins that may be made by the method of the invention are seen in Tables II and III.

TABLE II

```
ATGAAATTTAAAAAAACTATTGGTGCAATGGCTCTGACCACAATGTTTGTAGCAGTGAGT
---------+---------+---------+---------+---------+---------+  60
TACTTTAAATTTTTTTGATAACCACGTTACCGAGACTGGTGTTACAAACATCGTCACTCA
 M  K  F  K  K  T  I  G  A  M  A  L  T  T  M  F  V  A  V  S  -

GCTTCAGCAGTAGAGAAAAATATTACTGTAACAGCTAGTGTTGATCCTGTAATTGATCTT
---------+---------+---------+---------+---------+---------+ 120
CGAAGTCGTCATCTCTTTTTATAATGACATTGTCGATCACAACTAGGACATTAACTAGAA
 A  S  A  V  E  K  N  I  T  V  T  A  S  V  D  P  V  I  D  L  -

TGCAAGCTGATGGCAATGCTCTGCCATCAGCTGTAAAGTTAGCTTATTCTCCCGCATCA
---------+---------+---------+---------+---------+---------+ 180
AACGTTCGACTACCGTTACGAGACGGTAGTCGACATTTCAATCGAATAAGAGGGCGTAGT
 L  Q  A  D  G  N  A  L  P  S  A  V  K  L  A  Y  S  P  A  S  -

AAAACTTTTGAAAGTTACAGAGTAATGACTCAAGTTCATACAAACGATGCAACTAAAAAA
---------+---------+---------+---------+---------+---------+ 240
TTTTGAAAACTTTCAATGTCTCATTACTGAGTTCAAGTATGTTTGCTACGTTGATTTTTT
 K  T  F  E  S  Y  R  V  M  T  Q  V  H  T  N  D  A  T  K  K  -

GTAATTGTTAAACTTGCTGATACACCACAGCTTACAGATGTTCTGAATTCAACTGTTCAA
---------+---------+---------+---------+---------+---------+ 300
CATTAACAATTTGAACGACTATGTGGTGTCGAATGTCTACAAGACTTAAGTTGACAAGTT
 V  I  V  K  L  A  D  T  P  Q  L  T  D  V  L  N  S  T  V  Q  -

ATGCCTATCAGTGTGTCATGGGGAGGACAAGTATTATCTACAACAGCCAAAGAATTTGAA
---------+---------+---------+---------+---------+---------+ 360
TACGGATAGTCACACAGTACCCCTCCTGTTCATAATAGATGTTGTCGGTTTCTTAAACTT
 M  P  I  S  V  S  W  G  G  Q  V  L  S  T  T  A  K  E  F  E  -

GCTGCTGCTTTGGGATATTCTGCATCCGGTGTAAATGGCGTATCATCTTCTCAAGAGTTA
---------+---------+---------+---------+---------+---------+ 420
CGACGACGAAACCCTATAAGACGTAGGCCACATTTACCGCATAGTAGAAGAGTTCTCAAT
 A  A  A  L  G  Y  S  A  S  G  V  N  G  V  S  S  S  Q  E  L  -

GTAATTAGCGCTGCACCTAAAACTGCCGGTACCGCCCCAACTGCAGGAAACTATTCAGGA
---------+---------+---------+---------+---------+---------+ 480
CATTAATCGCGACGTGGATTTTGACGGCCATGGCGGGGTTGACGTCCTTTGATAAGTCCT
 V  I  S  A  A  P  K  T  A  G  T  A  P  T  A  G  N  Y  S  G  -

GTAGTATCTCTTGTAATGACTTTGGGATCCTGA      Seq. ID No. 2
---------+---------+---------+--- 513
CATCATAGAGAACATTACTGAAACCCTAGGACT
 V  V  S  L  V  M  T  L  G  S  *   -  Seq. ID No. 3
```

TABLE I-continued

| | | | | |
|---|---|---|---|---|
| ttaggtagtg | catccaatta | gtagaacatg | tgtttttcga | taaacgctcc | gatctctttt |
| tcgtggatct | caactgagcg | tgagaagcag | attgttttac | gagccaaccg | cttaatgcgg |
| gtgcgtagcg | tcagattatt | acgctcaatg | cgttgggtga | atattttgcc | ggtcagatgc |
| ttattcttcg | gtacc Seq. ID No. 1 | | | | |

The protein identified in Table II is referred to as CFA1 and was disclosed by Karjalainen, et al.

TABLE III

```
ATGTTAAAAATAAAATACTTATTAATAGGTCTTTCACTGTCAGCTATGAGTTCATACTCA
---------+---------+---------+---------+---------+---------+  60
TACAATTTTTATTTTATGAATAATTATCCAGAAAGTGACAGTCGATACTCAAGTATGAGT
 M  L  K  I  K  Y  L  L  I  G  L  S  L  S  A  M  S  S  Y  S  -

CTAGCTGCAGCGGGGCCCACTCTAACCAAAGAACTGGCATTAAATGTGCTTTCTCCTGCA
---------+---------+---------+---------+---------+---------+120
GATCGACGTCGCCCCGGGTGAGATTGGTTTCTTGACCGTAATTTACACGAAAGAGGACGT
 L  A  A  A  G  P  T  L  T  K  E  L  A  L  N  V  L  S  P  A  -

GCTCTGGATGCAACTTGGGCTCCTCAGGATAATTTAACATTATCCAATACTGGCGTTTCT
---------+---------+---------+---------+---------+---------+180
CGAGACCTACGTTGAACCCGAGGAGTCCTATTAAATTGTAATAGGTTATGACCGCAAAGA
 A  L  D  A  T  W  A  P  Q  D  N  L  T  L  S  N  T  G  V  S  -

AATACTTTGGTGGGTGTTTTGACTCTTTCAAATACCAGTATTGATACAGTTAGCATTGCG
---------+---------+---------+---------+---------+---------+240
TTATGAAACCACCCACAAAACTGAGAAAGTTTATGGTCATAACTATGTCAATCGTAACGC
 N  T  L  V  G  V  L  T  L  S  N  T  S  I  D  T  V  S  I  A  -

AGTACAAGTGTTTCTGATACATCTAAGAATGGTACAGTAACTTTTGCACATGAGACAAAT
---------+---------+---------+---------+---------+---------+300
TCATGTTCACAAAGACTATGTAGATTCTTACCATGTCATTGAAAACGTGTACTCTGTTTA
 S  T  S  V  S  D  T  S  K  N  G  T  V  T  F  A  H  E  T  N  -

AACTCTGCTAGCTTTGCCACCACCATTTCAACAGATAATGCCAACATTACGTTGGATAAA
---------+---------+---------+---------+---------+---------+360
TTGAGACGATCGAAACGGTGGTGGTAAAGTTGTCTATTACGGTTGTAATGCAACCTATTT
 N  S  A  S  F  A  T  T  I  S  T  D  N  A  N  I  T  L  D  K  -

AATGCTGGAAATACGATTGTTAAAACTACAAATGGGAGTCAGTTGCCAACTAATTTACCA
---------+---------+---------+---------+---------+---------+420
TTACGACCTTTATGCTAACAATTTTGATGTTTACCCTCAGTCAACGGTTGATTAAATGGT
 N  A  G  N  T  I  V  K  T  T  N  G  S  Q  L  P  T  N  L  P  -

CTTAAGTTTATTACCACTGAAGGTAACGAACATTTAGTTTCAGGTAATTACCGTGCAAAT
---------+---------+---------+---------+---------+---------+480
GAATTCAAATAATGGTGACTTCCATTGCTTGTAAATCAAAGTCCATTAATGGCACGTTTA
 L  K  F  I  T  T  E  G  N  E  H  L  V  S  G  N  Y  R  A  N  -

ATAACAATTACTTCGACAATTAAA
---------+----------+----504
TATTGTTAATGAAGCTGTTAATTT
 I  T  I  T  S  T  I  K  - Seq. ID No. 5
```

The DNA sequence of Table III has been designated as CS3 by Boylan, et al. (*Infect. Immun.* 56:3297–3300). The DNA sequences and the proteins encoded by those DNA sequences are identified for purposes of exemplification only. As previously indicated, other proteins produced under the control of a temperature-regulated promotor can be produced by the method of the invention.

It is also possible to add to the broth ingredients not specifically identified which are commonly used in the art such nutrients, antibiotic and trace elements to enhance production of the proteins. Other buffers, including, for example, citrate and carbonate buffering systems, may be used in the wash runs in the manner disclosed in the examples and the general methods.

What is claimed is:

1. A method of producing a protein which affects bacterial colonization under the control of temperature-regulated promotors in enteric bacteria comprising the steps of:

(1) inoculating a broth containing tryptone and yeast extract with bacteria containing a DNA sequence which encodes a protein under the control of a temperature-regulated promotor, (2) allowing fermentation at a temperature of less than 33° C. but more than 25° C. at least until the late logarithmic phase, (3) removing the bacteria from the media, then (4) recovering the desired proteins from the spent media.

2. A method of claim 1 wherein the protein produced is in *E. coli.*

3. A method of claim 2 wherein the protein produced is CS6 protein.

4. A method of claim 1 wherein the temperature range in step (2) is 30° C. to 33° C.

5. A method of claim 1 wherein, during the late logarithmic phase the temperature of the fermenting broth is raised to between 36° C. and 39° C.

6. A method of producing a protein which affects bacterial colonization under the control of temperature-regulated promotors in enteric bacteria comprising the steps of:

(1) inoculating a broth containing tryptone and yeast extract with bacteria containing a DNA sequence which encodes a protein under the control of a temperature-regulated promotor, (2) allowing fermentation at a temperature of less than 33° C. but more than 25° C. at least until the late logarithmic phase, (3) removing the bacteria from the culture media and suspending the bacteria in a solution, (4) disrupting the surface of the bacteria, (5) removing the bacteria and/or bacterial debris from the solution in which said bacteria are suspended, then (6) recovering the desired proteins from solution obtained in step 5.

7. A method of claim 6 wherein the protein produced is in *E. coli.*

8. A method of claim 7 wherein the protein produced is CS6 protein.

9. A method of claim 6 wherein the temperature range in step (2) is 30° C. to 33° C.

10. A method of claim 6 wherein, during the late logarithmic phase the temperature of the fermenting broth is raised to between 36° C. and 39° C.

* * * * *